US006585987B1

(12) United States Patent
Fransoni

(10) Patent No.: US 6,585,987 B1
(45) Date of Patent: Jul. 1, 2003

(54) COMPLEXES OF HYALURONIC ACID/CARNITINES AND PHARMACEUTICAL AND COSMETIC COMPOSITIONS

(75) Inventor: Michele Fransoni, Dublin 2 (IE)

(73) Assignee: Continental Projects Limited, Dublin (IE)

( * ) Notice: Subject to any disclaimer, the term of this patent is extended or adjusted under 35 U.S.C. 154(b) by 0 days.

(21) Appl. No.: 09/831,746

(22) PCT Filed: Nov. 11, 1999

(86) PCT No.: PCT/IT99/00364

§ 371 (c)(1),
(2), (4) Date: Jun. 25, 2001

(87) PCT Pub. No.: WO00/29030

PCT Pub. Date: May 25, 2000

(30) Foreign Application Priority Data

Nov. 13, 1998 (IT) .......................... MI98A2461
Jan. 15, 1999 (IT) .......................... MI99A0064

(51) Int. Cl.[7] .......................... A61K 7/00; A61K 31/70; A61K 31/95; C07C 229/00
(52) U.S. Cl. .......................... 424/401; 514/62; 514/561; 514/563; 562/567
(58) Field of Search .......................... 562/567; 514/561, 514/62, 563; 424/401

(56) References Cited

U.S. PATENT DOCUMENTS 5,442,053 A 8/1995 della Valle et al.
5,922,331 A 7/1999 Mausner

FOREIGN PATENT DOCUMENTS

| BE | 663 616 | 9/1965 |
| EP | 0 951 909 | 10/1999 |
| FR | 2609393 A1 * | 7/1988 |
| WO | WO95/05168 | 2/1995 |

OTHER PUBLICATIONS

Wenninger J. A.: "International Cosmetic Ingredient Dictionary and Handbook (vol. 3)", The Cosmetic Toiletry and Fragrance Association, Washington, p. 1878, column 2 1997.
Patent Abstracts of Japan vol. 1995, No. 07, Aug. 1995 & JP07 097401 (Shiseido Co Ltd), Apr. 1995.
Boehm K. A. et al.: "Carnitine: A Review for the Pharmacy Clinician" Hospital Pharmacy, US, Lippincott, Philadelphia, vol. 28, No. 9, Sep. 1993, pp. 843, 847–850.
Patent Abstracts of Japan vol. 014, No. 242, May 1990 & JP02 062814 (Chisso Corp), Mar. 1990.

* cited by examiner

Primary Examiner—Johann Richter
Assistant Examiner—Paul A. Zucker
(74) Attorney, Agent, or Firm—Nixon & Vanderhye P.C.

(57) ABSTRACT

Complexes of hyaluronic acid and carnitine of its derivatives and the simple combinations of them are useful in therapeutics and cosmetics. They have pharmacological activity, that is protective activity on tissues and cell plasma membrane, anti-inflammatory, radical scavenging activities and the like, was well as cosmetic activity, such as restoring or maintaining cutaneous elasticity.

26 Claims, No Drawings

COMPLEXES OF HYALURONIC ACID/CARNITINES AND PHARMACEUTICAL AND COSMETIC COMPOSITIONS

This application is a 371 of PCT/IT99/00364 filed Nov. 11, 1999.

The present invention relates to complexes of hyaluronic acid and "carnitines", the latter herein meaning both carnitine as it is and, more specifically, its acyl derivatives with straight or branched chain aliphatic carboxylic acids, optionally unsaturated or polyunsaturated, containing 2 to 20 carbon atoms.

Although the complexes according to the invention can contain, as carnitine component, DL-carnitine or D and L carnitine mixtures in variable ratios, as well as the related acyl derivatives as stated above, the preferred embodiment relates to complexes of hyaluronic acid and L-carnitine or acyl-L-carnitine, wherein "acyl" has the meanings defined above. In the present invention, "carnitine" will therefore mean, unless otherwise stated, L-carnitine; the same applies for the various acylcarnitines which will be cited in the following.

"Hyaluronic acid" will herein mean a hyaluronic acid of molecular weight ranging from about $2 \times 10^3$ to about $5 \times 10^6$, preferably from about $2 \times 10^5$ to about $3 \times 10^6$.

As it is obvious by what stated above, both components of the complexes according to the invention are per se known. Information concerning hyaluronic acid as well as numerous references concerning carnitine (page 281) and acetylcarnitine (page 13), can be found, inter alia, in *Merck Index*, $11^{th}$ edition, page 751, 281 and 13, respectively; whereas acylcarnitines and/or the use thereof are the object of a number of patents (see for example U.S. Pat. No. 4,346,107, U.S. Pat. No. 4,194,006, U.S. Pat. No. 4,343,816).

The therapeutical indications of the cited components are also well known. In particular, hyaluronic acid is used as coadjuvant in the treatment of synovitis and tissutal reparation processes.

It now has been found that complexes (or even simple combinations) of hyaluronic acid and "carnitines" (which means both carnitine as it is and its acyl derivatives) can be in the form of and act as an alimentary supplement or a real medicament, depending on their favourable, preventive or therapeutical action, which said complexes or combinations are intended to exert, depending on the specific end users.

Furthermore, it has been found that said complexes and combinations can be valuable in cosmetics.

The complexes and the combinations indicated above, have, in fact: a) enhanced protective activity on tissues and cell plasmamembrane; b) antiinflammatory and radical-scavenger activities; c) anti-aging activity, in particular restoring- or maintaining-activities on skin elasticity; d) a general trophic, cosmetically remarkable, action. In particular, the complexes and the combinations according to the invention are suitable for the treatment of synovitis and gonarthrosis, Crohn's disease, ulcerous rectocolitis and celiac disease. Said activities can be more or less marked, depending on the single "carnitine" used.

Therefore a further object of the invention are pharmaceutical and cosmetic compositions containing as active ingredient: a) combinations of hyaluronic acid and carnitine or acylcarnitine, or b)—according to a preferred aspect of the invention—complexes of hyaluronic acid and carnitine or acylcarnitine, said combinations and complexes containing the two components in weight ratios ranging from 3:1 to 1:3, preferably in equiponderal ratios.

More particularly, an object of the invention are pharmaceutical compositions containing as active ingredient the combinations a) or the complexes b) above defined, with protective activity on tissues and cell plasmamembrane; with antiinflammatory and radical-scavenger activities; for the therapy of synovitis and gonarthrosis; for the therapy of Crohn' disease, ulcerous rectocolitis and celiac disease; moreover, cosmetic compositions containing the combinations a) or the complexes b), with anti-aging activity, and restoring- and maintaining-activities on skin elasticity and general trophic action.

As already mentioned, carnitine and acylcarnitines contained in the above mentioned pharmaceutical and cosmetic compositions are preferably L-carnitine and acyl-L-carnitine. Particularly preferred are acetyl-L-carnitine, propionyl-L-carnitine and palmitoyl-L-carnitine.

The complexes of the invention contain the two components in weight ratios ranging form 1:3 to 3:1, preferably in equiponderal ratios. They are obtained by: a) addng hyalluroinic acid to a suspension or solution of acylcarnitine (or carnitine) in ethanol/PBS (phosphate-buffered saline), under stong stirring, at a temperature of 20–60° C., preferably about 50° C., or b) adding acylcarnitine (or carnitine) to a solution of hyaluronic acid in PBS, subjecting the shole first to sonication at temperatures ranging between 10 and 30° C., preferably at 15–20° C., thn to centrifugation, with recovery of the supernatant. The resulting product has been proved to be a real complex by means of the chemico-physical detrminations which will be described in the folwing.

The process for the preparation of the complexes of the invention is illustrated by the following non-limiting examples. In the following, hyaluronic acid will be referred to as HA. Furthermore, HA will mean a hyaluronic acid of molecular weight ranging from about $2 \times 10^5$ to about $3 \times 10^6$, both as the acid and as alkali or alkaline-earth metal salts.

Example 1

Palmitoyl-L-carnitine (PC) was dissolved in absolute ethanol, then the solution was added to a PBS solution (pH 7.4) so as to obtain PC final concentrations of 0.1 and 0.5 and 1 mg/ml. The resulting suspensions were vortexed for 3 min at room temperature then left under stirring for 1 hour at 50° C. During this time powder hyaluronic acid (HA) of different molecular weights ($2 \times 10^5$ to $3 \times 10^6$), was slowly added to the suspension to an HA final concentration of 0.1, 0.5 and 1 mg/ml. At each addition of HA the sample was vortexed for at least 1 min and subsequently incubated under the same temperature conditions.

Example 2

Powder PC was added to a PBS solution and then the resulting suspension was sonicated in the cold for a time ranging from 5 to 15 minutes. HA was subsequently added and the resulting mixture was vortexed for some minutes, then incubated under stirring for about an hour at temperatures ranging from 210 to 50° C.

Example 3

To a 2 ml solution of HA with molecular weight $3.4 \times 10^6$ or $2 \times 10^5$, respectively, in PBS (1 mg ml$^{-1}$) was added an aliquot of PC (20 µM) in ethanol (20 µL). The components were mixed for 15–20 min at 20° C. in an ultrasonicating water-bath, set at 100W. The resulting opalescent solutions were centrifuged (3000 g) for 10 min and the supernatants separated. This solution showed no evidence of phase separation even after standing at 4° C. for several days.

EVALUATION OF HA/CARNITINE COMPLEX

Determination of the Effects of Ultrasonication on the Molecular Dispersity of HA.

In order to determinate the effects of ultrasonic on HA alone, the protocol used above (Example 3) was repeated for periods of up to 2 h in the absence of PC. An aliquot (0.5 ml) of resulting sonicated or unsonicated (1 mg ml$^{-1}$) in PBS (pH 7.2) containing 20 μl of ethanol was then applied to a Sepharose CL-2B gel filtration column (30×1 cm) equilibrated with the same buffer. The column was eluted at 3–6 ml/h with PBS and the levels of Ha in the collected fractions were determined by hexuronate analysis using the Blumenkranze and Asboe-Hansen method.

Studies on the Interaction of HA with $^3$H-PC by Gel Exclusion Chromatography.

Mixtures of HA (1 mg ml$^{-1}$ in PBS) and ethanolic $^3$H-PC (20 μl; 20 μM) were sonicated for 2 h using the protocol described above. Sonicates (1 ml) were fractionated on a Sepharose CL-2B column (1×60 cm) eluting at 3.6 ml h$^{-1}$ with PBS as the elution buffer. Fractions (1 ml) were collected and monitored for hexuronic acid and radioactivity (disintegration per minute) by scintillation spectrometry.

Studies on the Interaction of HA with PC using MALLS Photometry.

In these experiments, a MALLS photometer was used in conjunction with a refractive index (RI) detector, superose 6 HR30 gel permeation column (GPC) and dual piston reciprocating pump P500. Mixtures of HA (1.0 mg ml$^{-1}$ in PBS) and PC (20 μl; 20 μM in ethanol) were sonicated for 0, 15, 30, 60, or 120 min. Solutions were then diluted with an equal volume of PBS, centrifuged (3000 g) and the supernatant applied to the Superose 6 column eluting at 24 ml h$^{-1}$ with PBS buffer using the P500 pump. Fractions were examined serially with the MALLS photometer and RI detector. All experiments were conducted in triplicate. The number-average molecular weight ($M_n$), weight-average molecular weight ($M_w$), Z-average molecular weight (Mz) and calculated root mean square (RMS) radii for each of these parameters were determined from the quantity of angular variation of scattered light for the fractions eluting from the column. The ratio $M_w/M_n$ was used to assess molecular polydispersity.

$^1$H-NMR Spectroscopy

High-resolution 1H-NMR (199.5 Mhz) of samples were obtained using a JEOLFX-200 spectrometer operating in the Fourier transform mode. Samples were contained in 10 mm Wilmad glass tubes together with a coaxial 5 mm tube containing tetramethyl silane in deuterium oxide. This was used as an external integration reference. The sample temperature was maintained at 37° C. All sample were degassed with argon prior to measurements. The conformational mobility (flexibility) of solution of HA was determined using a method that required determination of the linewidth at half-peak height ($\_v_{1/2}$) for the methyl proton resonance of the acetamidodeoxyglucose residues of the hyaluronate 1 H-NMR spectra.

$^{13}$C-NMR Spectroscopy $^{13}$C-NMR proton-decoupled spectra (50.1 Mhz) of HA preparations (10% w/v) dissolved in $D_2O$, were obtained using a JEOLFX-200 FT spectrometer. Samples were contained in 10 mm Wilmard glass tubes in which a 4 mm coaxial tube containing acetonitrile as an external reference had been placed. The sample temperature was maintained at 37° C. and a spectral width of 1 kHz and 6000 data points were used.

RESULTS

Gel Exclusion Chromatography of Sonicates of HA with 3H-PC.

Chromatography of sonicates HA with $^3$H-PC using the same conditions as used for HA alone showed that, while the majority of radioactively labelled PC appeared at the total volume ($V_L$), a portion of the applied radioactively labelled PC eluted at $V_0$. The $^3$H-PC eluted in fractions largely corresponding to the higher-molecular-weight fractions of HA.

Studies on the Effects of PC and Sonication on the Molecular Characteristics of HA using MALLS Photometry.

Although sonication of HA progressively decreases Mn, Mw and Mz with respect to unsonicated (native) HA (Mw= 3.4×10$^6$) these parameters were higher in the corresponding sonicates in which PC was included. The corresponding RMS radii were also consistently higher than in HA sonicates without PC but the polydispersity ($M_w/Mn$) was independent of the presence of PC or sonication time.

NMR Studies.

The $^{13}$C-NMR chemical shift values for HA shown that the values for the ring carbons of the N-acetylglucosamine and glucuronic acid disaccharide repeat unit of HA were comparable for all preparations confirming identical primary structures. Sonication of a high-molecular-weight HA or a low-molecular-weight HA preparation with PC for time periods up to 2 h markedly increased the proportion of flexible domains present, as determined from linewidth values of the acetamidomethyl protons in their respective $^1$H-NMR spectra. In the control experiments in which PC was omitted and sonication undertaken for the same periods of time, a slight decrease in the percentage of flexibility of the HA preparations was observed.

The effects of varying the HA concentrations on the percentage of flexible and rigid segments present in HA solution sonicated for 60 min in the presence of PC showed that the relative proportions present did not substantially change over a tenfold dilution range.

ANTIINFLAMMATORY ACTIVITY

A specific cutaneous inflammatory reaction, caused by different phlogogenic factors both of exogenous and endogenous origin, including the formation of free radicals, lipoperoxides, prostaglandins and cytokines, is that induced by intradermal injection of dithranol, as described by Mustakallio (Mustakallio K., DERMATOVENER, 54, 125, 1979).

Dithranol is intradermally injected at the dose of 20 mcg on the back of shaved Guinea pigs.

On the opposite side of the back, before the injection of the same amount of dithranol, HA alone or acetyl-L-carnitine (AC) alone, or HA and AC together or the HA and AC complex, are spread.

A mixture of lanolin and ethylene glycol monostearate was used to spread these compounds. After 48 hours of this treatment, the evaluation of the cutaneous inflammatory area induced by dithranol proved that HA is able to inhibit the inflammation area of about 30%. On the contrary, AC alone does not have protective activity.

The combination of AC and HA induces a more evident inhibitory effect on dithranol-induced inflammation.

The simultaneous administration of AC and HA induces an inhibitory effect at the surface of the inflammatory area of about 50%. A very significant inhibition (over 75%) is overall evident when the HA complex containing the same amount of HA and AC is used.

These experiences proved the surprising and powerful protective effect induced by the complex HA/AC compared with that exerted by the single compounds alone or together (Table 1).

This surprising, unexpected effect exerted by the complex of HA and AC compared with its components used either alone or together, has been demonstrated by a further, different test, that of theleocidin, which as other sorbolmyristates, if injected, induces in mice skin important alterations and the formation of tumoral reactions (Fujiki H., Biochem. Biophys. Res. Commun., 90. 976, 1979). These skin alterations increase the ornithinedecarboxylase enzyme, and this increase is related to the severity of the induced cutaneous damage.

In these experiences, theleocidin is injected on mice back shaved skin at a dosage of 5 mcg/mouse dissolved in 0.2 cc of solution.

HA and AC either administered alone, or together or in the form of a complex according to the invention, are spread five minute's before theleocidin on the backs of the animals. Ornithinedecarboxylase is dosed on the homogenised epidermis of the animals five hours after the theleocidin injection, according to the method by O'Brien and Nakadate (O'Brien T. G., Cancer Res., 35, 1662, 1975—Nakadate T. Cancer Res., 42, 2841, 1982). Protein concentration of an epidermis extract is evaluated following the method described by Lowry (Lowry O. H., J. Biol. Chem., 193, 265, 11951).

As shown in Table 2, these experiments also prove a surprising, unexpected and more powerful effect of the complex of HA and AC according to the invention compared with the two separate components.

TABLE 1

Antiinflammatory activity on Dithranol induced inflammation

| Treatment | % inhibition of phlogistic area compared with controls |
|---|---|
| AC 50 mg | 9 ± 0.19 |
| AC 100 mg | 14 ± 0.34 |
| HA 10 mg | 39 ± 1.6 |
| HA 50 mg | 38 ± 2.9 |
| AC 100 mg + HA mg 50 | 52 ± 4.9 |
| Complex HA/AC 50 mg | 65 ± 5.1 |
| Complex HA/AC 100 mg | 78 ± 6.8 |

TABLE 2

Increase of ornithinedecarboxylase activity induced by theleocidin

| Treatment | ornithinedecarboxylase activity (nmol of $CO_2$/60 min./mg protein) |
|---|---|
| AC 50 mg | 5 ± 0.45 |
| AC 100 mg | 11 ± 1.49 |
| HA 10 mg | 21 ± 2.8 |
| HA 50 mg | 31 ± 4.1 |
| AC 100 mg + HA 50 mg | 41 ± 4.9 |
| Complex AC/HA 50 mg | 55 ± 5.7 |
| Complex AC/HA 100 mg | 75 ± 6.9 |

CLINICAL TRIALS

EFFECT OF HYALURONIC ACID/CARNITINE ON THE BARRIER FUNCTION OF CORNEAL EPITHELIUM IN CASE OF "DRY EYE" SYNDROME

Dryness of the conjunctiva, isolated or in association with other ocular or extra-ocular disease, is recognizedly capable of inducing local damage on corneal epithelium which can, inter alia, lose its barrier function. On the basis of a preliminary experience on rabbits, which proved the efficacy of a 1:1 w/w combination of hyaluronic acid/carnitine in the prevention of erosions induced by iodine vapours, a clinical trial was carried out on 27 patients suffering from "dry eye" treated with either only hyaluronic acid or hyaluronic acid/carnitine. According to the protocol, each patient received for 4 weeks a medication (hyaluronic acid) in the form of collyrium in one eye and a different treatment (hyaluronic acid/carnitine) in the other eye, so that each patient also acted as the control. Subjective evaluation and clinical examinations, associated with a fluorescein test, were carried out 2 weeks after the beginning of the treatment as well as at its end (4 weeks). The obtained results proved that hyaluronic acid alone did not provide significant advantages either in improving the symptoms affecting the patients or in keeping and effective barrier function in corneal epithelium. Conversely, fluorophotometry of the eye treated with hyaluronic acid/carnitine in order to evaluate fluorescein uptake in specific corneal areas, showed a significant improvement of the barrier function already after 2 weeks of treatment in the cornea lower areas and 4 weeks in the central ones.

EVALUATION OF THE EFFICACY OF THE COMBINATION HYALURONIC ACID/CARNITINE IN THE TREATMENT OF TROPHIC ULCERS OF LOWER LIMBS

Vascular ulcers of lower limbs are multidisciplinary pathologies.

By ulcer, the loss of substance related to hemodynamic, hemorheological and coagulation changes is meant: the involvement of micro-circulation, either primary or secondary, is important in ulcer genesis, and it causes an impairment of tissue trophism, with loss of tissue.

Ulcers are often the manifestation of a number of pathologies underlying an insufficient blood circulation which causes hypoxia. Transcutaneous oximetry in fact evidenced that, in case of vascular-lesions, $pO_2$ reaches 5–10 mm Hg, levels capable of greatly affecting cell metabolic capabilities and energy production. Furthermore, leukocytes proliferate and exert their phagocytic activity at $pO_2$ of 30–40 mm Hg.

Therapy is a still unresolved problem, notwithstanding the great number of pharmacological and physical aids.

From the statistical point of view, according to numerous studies, lower limbs trophic ulcers affect 1–3% of population, with a 5% maximum among subjects older than sixty. The most common factors causing ulcers are phlebopathies, arteriopathies, diabetes with the related microangio-neuropathy. The affected areas are, in frequency order, ankle medial face, followed by ankle side face, front and rear face, calf and feet. The mean duration of an ulcer is about 26 weeks, with a range varying from 4 to 30 years, and relapses are very frequent.

The healing process involves inflammation with cell a migration, neovascularization and regeneration; cell reparation is mediated by various factors acting as tissue regeneration stimulators.

It is fundamental the observation of ulcer characteristics in order to foresee its evolution, and particularly important is the characterization on the basis of: site—shape—size—number—edges—granulation tissue—periulcerative epidermidis.

VENOUS ULCERS: They are more or less deep ulcerations related to hypertension secondary to varicose disease or venous thrombosis. Primum movens is chronic venous hypertension which affects microvessels with consequent circulation slowing down and structural and functional modifications.

ARTERIAL ULCERS: they are mostly related to peripheral atherosclerotic disease. Ulcerations are trophic lesions affecting subjects with chronic obliterans arteriosclerosis. They appear when a decrease in blood flow higher than 50%, in which condition compensation by microcirculation is no longer possible and the already precarious hemodynamic equilibrium is endangered.

The used protocol is the following one:

1) Topical administrations of a combination of hyaluronic acid and carnitine (1:1 by weight), or of carnitine alone or of hyaluronic acid alone, previous humidification of the lesion with saline for a time of 10 minutes. In the first treatments, it is possible to use hyaluronic acid at a higher concentration than carnitine, to promote ulcer cleansing. In the following treatments, such concentrations of the two molecules have been used as to better make use of the role of carnitine in normalizing tissue trophism. Treatment usually started during hospitalization and was subsequently continued at the nalgesic therapy clinic.

As a rule, patients undergo such treatment without problems; some subjects episodically suffered from slight, short irritations and sometimes from local burning during the first sessions of the treatment.

Patients enrolled in this trial came from Medicine and Surgery Departments, where they unsuccessfully received various medical treatments (mesoglycan, Connectivine, mucopolysaccharides).

18 females and 12 males were treated, of age from 62 to 80 years, with trophic ulcers of various size and at different sites, anyhow on limbs or feet.

RESULTS

Results were scored as follows: VERY GOOD, when the ulcer healed completely; GOOD, when an at least 50% reduction of the lesion was attained; NULL, when no significant changes of the lesion occurred after 30 day-treatment.

Results were as follows:

VERY GOOD: in 15 patients, i.e. 50%;

GOOD: in 11 patients, i.e. 36.7%

NULL: in 4 patients, i.e. 13.3%.

In case of the treatment with hyaluronic acid alone or with carnitine alone, results were remarkably poorer, in that in only 16% of the patients treated for the same time with hyaluronic acid a response which scared GOOD was obtained, whereas in no patients a VERY GOOD response was observed. Furthermore, from the histological point of view, biopsies from patients treated with the combination hyaluronic acid/carnitine showed a normalization of the epidermis layer which could not be observed in controls.

Finally, the use of the combination hyaluronic acid/carnitine proved a therapeutical efficacy even in the chronic ulcerations, i.e. those present for at least one year. After 23 weeks, 89% of the lesions more difficult to heal were completely closed, compared with 15% of those treated with the traditional therapy, which mainly consisted in exerting pressure, using hyaluronic acid and keeping the lesion humid.

No complications substantially occurred, considering the above mentioned symptoms.

CONCLUSIONS

In view of the obtained results, it can be stated that the treatment protocol suggested is completely satisfactory in almost all of the patients and such evidence is even more significant considering that previous medical treatment had not exerted favourable results. The four patients in which no results (NULL) were obtained, were successfully subjected to skin transplant.

SICKLE CELL ANEMIA

The cases described in the following relate to some subjects, suffering from drepanocytic anemia, a hemoglobinopathy common in African populations from malarial regions, in which large ulcerative areas with loss of substance are evident in lower limbs.

The term sickle cell anemia comprises a large group of hematologic disorders with different symptoms and genotypes. The most common form is the homozygous inheritance for hemoglobin S (deriving by the substitution of valine with glutamic acid in the 6 position of the β-hemoglobin chain). More rarely, sickle cell anemia is due to double heterozygosis for hemoglobin S and for thalassemia or for hemoglobin C. The formation of intracellular fibres, deriving from the polymerization of hemoglobin S, causes the typical sickle deformation of red blood cells. This results in rigidity of red blood cell, which causes to impairments of microcirculation and vaso-occlusion. Furthermore, such structural changes lead to reduced survival of red blood cells and therefore to chronic hemolytic anemia.

Clinical Manifestations

Sickle cell anemia appears within the two first years of life. Symptoms can be divided in two main categories, those related to hemolysis and those deriving from vaso-occlusive events. Therefore, torpid vascular ulcers usually resistant to the traditional therapeutical treatments are easily observed in these patients.

Treatment

Treatment carried out in these subjects with the combination hyaluronic acid/carnitine results in extremely favourable therapeutical results, with "restitutio ad integrum" of the damaged area within relatively short times.

HA/CARNITINE ANTIWEAR ACTIVITY

METHODS

Principle

A standard wear test used by engineers for many decades is the four-ball test, (Institute of Petroleum). Extreme pressure properties: friction and wear tests for lubricants. Four ball machine. In: Standard Methods for Analysis of Petroleum and related Products, Volume I. Chichester, Wiley, 1990, pp. 256). Its formal description as a simple test for anti-wear properties of industrial oils and greases "under extreme pressure"—i.e., extreme pressure by engineering standards- indicated that it could be many orders of magnitude too severe for a biological lubricant when comparing typical loads encountered in engineering and physiology. It was therefore most surprising and welcome when preliminary runs showed that synthetic synovial fluid not only survived the tests, but outperformed several industrial lubricants, (Hills B. A. Hyaluronic acid lubricating compounds. Australian patent #620821, 1992). This test was therefore adopted as an extreme test needed to differentiate anti-wear capabilities.

Four-Ball Test

The "four-ball extreme-pressure lubricant machine" has been described in standard test procedures (see above reference). If lubrication is poor under these extreme loads (40 kg vertical load) or breaks down after a time, then the fourth ball welds to the other three, and the test is stopped automatically. Otherwise the run is continued for 1 hr, and the diameters of the scars in each of two planes worn in each of the three fixed balls are measured by a travelling microscope in two mutually perpendicular planes. The results are reported as the mean of the six values obtained—the mean scar diameter (MSD). The sliding speed is 23.3 cm/sec for an initial Hertz stress of 3,400 MPa reducing to about 700 MPa for a typical MSD of 0.8 mm; this value corresponds to a wear asymmetry volume of about $2\times10^{-2}$ mm$^3$ (Willermet P. A. and Kandah S. J., Wear asymmetry—A comparison of the wear volumes of the rotating and the stationary balls in the four-ball machine. Trans.Am.Soc.Lubricating Eng. 26:173–178, 1982). The test is repeated three times on each sample. The best lubricating oils give values of about 0.35 mm, whereas the best aqueous lubricants have a typical range of about 0.8–0.9 mm (Castrol Mean Scar Diameters for Typical Commercial Lubricants. Sidney: Castrol (Australia) Pty.Ltd). Poor lubricants such as water or saline do not complete the test; the balls weld together after only 10–12 sec.

Materials

The following fluids were tested:
1. Synovial fluid was aspirated from the knee joint of human volunteers. Fluid with any trace of blood was discarded. The fluid from all Joints was pooled to acquire the 9 ml needed for each test and was immediately used for the assay. The pH range of the pools was 6.5–6.9.
2. A solution of Hyaluronan (10 mg/ml; Healon, LKB-Pharmacia) was buffered to pH 6.7.
3. A solution of carnitine or its acyl-derivatives (i.e. acetyl-, propionyl-, palmitoyl-, etc.) was buffered to pH 6.7.
4. A synthetic synovial fluid was prepared by using different amounts of HA and carnitines. For example, 10 mg/ml HA and 10 mg/ml carnitine or its derivatives were mixed and buffered to pH 6.7.

TABLE 3

Mean scar diameters

| FLUID | MSD* (mm) | n |
|---|---|---|
| Synovial fluid | 0.66 ± 0.02 | 11 |
| HA | n.d. | 11 |
| L-Carnitine | n.d. | 11 |
| Acetyl-L-Carnitine (ALC) | n.d. | 11 |
| Propionyl-L-Carnitine (PLC) | n.d. | 11 |
| Palmitoyl-L-Carnitine (PaLC) | n.d. | 11 |
| HA + L-Carnitine | 1.57 ± 0.12 | 11 |
| HA + ALC | 0.67 ± 0.01 | 11 |
| HA + PLC | 0.59 ± 0.02 | 11 |
| Ha + PaLC | 0.51 ± 0.01 | 11 |

*Mean = SEM

Results and Discussion.

Since lubricants that reduce friction do not necessarily reduce wear, we have addressed the new property of a chemical association between HA and derivatives to decrease significantly wear.

The value for synovial fluid approached that for the best lubricating oils, 0.35 mm, and exceeded values for "base stock" lubricating oils; even more impressive was the fact that the MSD of 0.66 mm was less than that of any aqueous-based commercial lubricant. Whereas HA or carnitines alone had no evident anti-wear capabilities under these conditions, when using HA with carnitine derivatives, an MSD value similar to the value measured for synovial fluid was found. For example, in presence of Palmitoyl-L-carnitine and HA a value of 0.51 mm was obtained. Statistical analysis showed no significant difference between the values for acetyl-, propionyl-, or palmitoyl-L-carnitine, although the results with palmitoyl-L-carnitine were the rather best. On the other hand, carnitine and HA showed a worse MSD value of 1.57 mm demonstrating that the acyl-residues were important for the anti-wear properties.

The MSD values for the mixture of HA plus carnitine derivatives could be attributable only to the acquisition of synergism between the two components. Moreover, when measuring coefficient of kinetic friction under load, the same mixture showed a superb lubricant property, giving coefficients of kinetic fraction as low as 0.002–0.005 under high load, i.e. within the physiological range.

TROPHIC PROPERTIES OF HA/CARNITINE ON CARTILAGE TISSUE

Materials and Methods

Cartilage Tissue Sampling

Thirty-five subjects were included in the study. Exclusion criteria were septicaemia, connective tissue disordes, rheumatoid arthritis, crystal deposition diseases, known hereditary or congenital defects, immobilization for several weeks as well as treatment with corticosteroids and cytotoxic drugs.

Culture Procedures

Tissue specimens obtained from each donor were cut into pieces of 3–6 mg in Dulbecco's modified Eagle's medium (DMEM) supplemented with penicillin (5.000 i.u. ml$^{-1}$) The tissue was washed 3 times with this culture medium. Cartilage pieces were taken at random, weighed and distributed into the different wells of multiwell culture plates (typically between 30 and 60 mg tissue/well). Extra pieces were not cultured but stored at $-20°$ C. in order to assess the initial proteoglycans (PG) and HA contents of the cartilage. Culture medium supplemented with 20% (v/v) foetal calf serum (culture medium A) was then added to each well and the culture plates were placed in a 90%: 10% (v/v) air: $CO_2$ humidified incubator for 48 h at 37° C.

For each experiment the cartilage from one individual was used and tissue cultures were conducted in triplicate: that is, for the control culture as well as for each HA, Acetyl-carnitine (ALC) or HA+ALC, 3 cartilage explants were cultured separately. Reported values are the mean of the triplicate cultures.

Pulse studies

After 2 day of culture, the culture medium was aspirated and the explants were washed 3 times with 1 ml of DMEM. Explants were resuspended in 5% FCS culture medium (1 ml 50 mg$^{-1}$ tissue) supplemented with $^3$H-glucosamine (50 $\mu$Ci ml$^{-1}$) (culture medium B). To each well, a solution of HA, Acetyl-carnitine (ALC) or HA+ALC, was added (10 ml/ml in culture medium) to achieve the final concentration of 100 $\mu$g of HA and 100 $\mu$g of ALC. Control culture received medium alone. Culture wells were then incubated for 12 h.

Chase Studies

After one day of culture in medium A, the cartilage pieces were aspirated free of medium, washed 3 times with 1 ml of DMEM, resuspended in culture medium B (1 ml 50 mg$^{-1}$ tissue) and cultured for 12 h. After pulse labelling, the cartilage pieces were washed with DMEM and resuspended in culture medium A. Medium alone or the appropriate molecules (HA, ALC or HA+ALC) dissolved in medium were added to each well (10 $\mu$l ml$^{-1}$) as stated above and a non-radioactive chase period was conducted for 24 h.

Isolation and Purification of Hyaluronan and Proteoglycans

At the end of the pulse labelling and non-radioactive chase periods, the culture media were removed and the cartilage pieces were washed with 0.15 M sodium chloride/ 0.05 M sodium acetate, pH 6.0 (buffer A). Media and corresponding washes were combined. Bovine nasal PGs (500 $\mu$g ml$^{-1}$) and hyaluronan (10 $\mu$g ml$^{-1}$) were added. The mixtures were dialyzed against buffer A and then incubated with papain (10 mg ml$^{-1}$) for 24 h at 60° C. Cartilage specimens were resuspended in buffer A; papain was added to each vial (0.1 mg/ ml$^{-1}$) and the tissue were digested for 24 h at 60° C. Aliquots were sampled for hydroxyproline determinations or subjected to ion-exchange chromatography on Econo-Pak Q cartridge.

The Econo-Pak Q column (5 ml) was pre-equilibrated in buffer A at a flow rate of 2 ml min$^{-1}$. Aliquots of papain-digested samples (100–200 $\mu$l for tissue digest and 0.5–1 ml for medium digests) were adjusted to 2 ml with buffer A and applied to the column that was then washed with 6 column volumes of buffer A. Anionic macromolecules were eluted from the column at 2 ml m$^{-1}$ with the following NaCl gradient (0.15–0.23 M over 2 min run, 0.23–0.23 M over 15 min, 0.23–1.5 M over 15 min) in 0.05 M Na acetate pH 6.0. Fractions of 2 ml were collected and assayed for radioactivity. The yield of radioisotope in the combined breakthrough and gradient fractions was >90%.

Two $^3$H-radiolabelled peaks were consistently eluted from the column: peak A at 0.23 M NaCl and peak B at about 1 M NaCl. For each specimen (tissues and media) fractions containing radiolabelled peaks were separately pooled, heated at 80° C. for 10 min and applied to a column (0.7×50 cm) of Sephadex G-50 equilibrated in 0.1 M ammonium bicarbonate buffer, pH 8.5. In each case more than 90% of the radiolabelled material present in both peaks A and B eluted at the excluded volume of the G-50 column. Therefore, aliquots of peaks A and B were digested with Streptoimyces hyaluronidase (0.1 u/aliquot in 0.05 M Na acetate pH 5.0, 6 h at 60° C.) and chondroitinase ABC (0.5 u/aliquot in 0.1 M TRIS-fluoride, pH 8.0, 6 h at 37° C.) and the digestion products were applied to the G-50 column. On the other hand, the digestion products of chondroitinase ABC are also included into the G-50 column but, in contrast to Streptomyces hyaluronidase, chondroitinase ABC digest both HA and chrondroitin chains. Accordingly, the amount of [$^3$H]-HA present in each peak was calculated by multiplying the total radioactivity of the peak by the relative percentage of radiolabelled material that was sensitive to Streptomyces hyaluronidase whereas the amount of [$^3$H]-PG present in each peak was calculated by multiplying the total radioactivity of the peak by the relative percentage of radiolabelled material that was resistant to digestion Streptomyces hyaluronidase and susceptible to digestion with chrondroitinase ABC.

Analytical Methods

Hydroxyproline was determined by the method of Woessner and hexuronate acid by the method of Bitter & Muir. HA was quantified by a specific radiosorbent assay technique.

Expression of Results and Statistics.

The rate of biosynthesis of PG and HA was determined by the summation of [$^3$H]-PG and [$^3$H]-HA disintegrations per min (d.p.m.) found in the papain-digested tissues and media at the end of the 12 h pulse labelling period and expressed as d.p.m. [$^3$H]-PG and [$^3$H]-HA per h and per mg of hydroxyproline. Indeed, the loss of hydroxyproline (and thus of collagen) from tissue specimens into the medium over a 72-h culture period was less than 5% of the amount present in cartilage pieces before culture. At the end of the 24-h non-radioactive chase period, the total incorporation of [$^3$H]-glucosamine into HA and PGs was determined by the summation of [$^3$H]-HA and [$^3$H]-PGs d.p.m. found in the media and corresponding papain-digested tissue specimens. The statistical significance of the differences observed between groups was evaluated by the Mann-Whitney U test whereas in each group the significance of the differences in PG and HA metabolism in the presence of different concentrations of Carnitine±HA were evaluated by the Wilcoxon signed-ranks test.

Results and Discussion

The PG and HA contents of cartilage specimens were distributed over a wide range of values (mean±s.d.= 0.77±0.09 and 0.05±0.03 for the PG and HA contents, respectively). In the different pulse and chase experiments conducted in the absence and in the presence of the compounds to test, analysis of tissue and media samples gave the following results: 50–70% of the labelled material present in peak A was sensitive to Streptomyces hyaluronidase and was thus identified as [$^3$H]-HA. On the other hand, all the labelled material present in peak B was identified as chondroitin sulphate (and thus as proteoglycans) as it was consistently resistant to digestion with Streptomyces hyaluronidase and susceptible to complete digestion with chondroitinase. In the absence of HA and/or Acetyl-L-Carnitine (ALC)., the rates of PG and HA synthesis were distributed over a specific range of values (38.11±8.1 for PG Synthesis and 3.9±0.8 for HA synthesis). When labelled cartilage explants were cultured in the absence of drugs the net loss of [$^3$H]-HA and [$^3$H]-PG molecules was 33.5±7.3 and 25.3±5.9 respectively.

In presence of HA or acetyl-carnitine alone, a slight increase of PG and HA synthesis was observed but only the presence of both molecules at the same time was able to significantly increase the synthesis of PGs and HA (Table 4). In normal cartilage 100 $\mu$g of HA and ALC respectively produced a statistically significant increase in the tissue content of labelled HA and PGs (p<0.001). Moreover, HA plus ALC did induce a significant change in the net loss of labelled PGs and HA (p<0.01) from cartilage during the 24 h chase period (Table 5) while HA or ALC alone reduced only the net loss of labelled HA.

These results provide for the first time evidence that in articular cartilage the chemical association of HA and ALC is able concomitantly to increase HA and PGs synthesis and reduce the loss of newly synthesized HA molecules from the tissue. Indeed, the negative metabolic balance of HA leads to osteoarthritis (OA) like changes in the normal articular tissue as the OA cartilage matrix is characterized by a progressive depletion of its content in HA. Accordingly, the increase of PG synthesis without any reduction in the net loss of PGs is a beneficial effect since the decrease in the concentration of PGs is proportional to the severity of the OA process.

TABLE 4

| Incubation mixture | PG synthesis d.p.m. [$^3$H] PG × 10$^3$/h/mg OH/proline | HA synthesis d.p.m. [$^3$H] HA × 10$^3$/h/mg OH/proline |
| --- | --- | --- |
| Control | 38.11 ± 8.3 | 3.9 ± 0.8 |
| HA | 39.2 ± 9.2 | 4.5 ± 0.93 |
| ALC | 38.73 ± 7.9 | 4.1 ± 1.0 |
| HA/ALC | 69.3 ± 8.5 | 6.97 ± 0.9 |

TABLE 5

| Incubation mixture | % of radiolabelled molecules recovered in the media | |
| --- | --- | --- |
| | [$^3$H] PG Loss/24 h | [$^3$H] HA Loss/24 h |
| Control | 25.3 ± 5.9 | 33.5 ± 7.3 |
| HA | 20.1 ± 7.5 | 28.0 ± 6.09 |
| ALC | 24.9 ± 6.7 | 29.05 ± 8.30 |
| HA/ALC | 5.9 ± 3.1 | 11.0 ± 2.1 |

The addition of the two components separately (in this case any chemical interaction is extremely unlikely or random in aqueous environments in which the molecules are added) did not reveal any agonistic effect of the two substances. On the other hand, the kinetic of dissociation of the chemical interactions between HA and Carnitine derivatives obtained in suitable in vitro conditions is, also in presence of water, extremely slow and it seems to be related to the presence of acyl residues. This implies that any boundary lubrication of the Joint is really a subtype known in engineering as "lamellated solid lubrication". Finally, the additional biological effects present in our compound compared to the simple combination of the two products is probably related to the presence of this new chemical species into the cell microenvironment.

Examples of pharmaceutical compositions according to the invention are reported in the following.

1–2 ml vials for intraarticular injection, containing:
- A) 2–5 mg of HA+2–5 mg of L-carnitine (or acetyl-, propionyl-, palmitoyl-L-carnitine); or
- B) 4–10 mg of 1:1 (w/w) complex HA/L-carnitine (or HA/acetyl-, propionyl-, palmitoyl-L-carnitine); said injection being administered one or more times a week;

capsules for the oral administration, containing:
- C) 0.5–2 g of HA+0.5–2 g of L-carnitine (or of acetyl-, propionyl-, palmitoyl-L-carnitine); or
- D) 1–4 g of 1:1 (w/w) complex HA/L-carnitine (or HA/acetyl-, propionyl-, palmitoyl-L-carnitine); said tablets being administered 1–3 times a day in case of Crohn's disease, ulcerous rectocolitis, celiac disease;

gel for the topical administration, containing
- E) 1–5% of HA+1–5% of L-carnitine (or acetyl-, propionyl-, palmitoyl-L-carnitine); or
- F) 2–10% of 1:1 (w/w) complex HA/L-carnitine (or HA/acetyl-, propionyl-, palmitoyl-L-carnitine) to be applied 1–3 times a day on the inflammatory area.

Examples of cosmetic compositions according to the invention are gels similar to E) and F), or lotions, creams, beauty masks and the like, containing similar amounts of the two components hyaluronic acid/L-carnitine (or acetyl-, propionyl- or palmitoyl-L-carnitine) or, preferably, of the corresponding complexes according to the invention.

What is claimed is:

1. A process for preparing a complex of hyaluronic acid with carnitine or an acylcarnitine, comprising
   (a) mixing carnitine or acylcarnitine and hyaluronic acid together in a solvent of ethanol and/or phosphate-buffered saline,
   (b) sonicating the mixture of step (a);
   (c) centrifuging the sonicated mixture of step (b) into two phases, and discarding the upper phase; and
   (d) recovering the complex.

2. A complex of hyaluronic acid with a compound selected from the group consisting of carnitine and acylcarnitines produced by the process of claim 1.

3. A complex of hyaluronic acid with a compound selected from the group consisting of L-carnitine, acetyl-L-carnitine, propionyl-L-carnitine and palmitoyl-L-carnitine produced by the process of claim 1.

4. A complex as claimed in claim 2 wherein the two components are present in weight ratios from 1:3 to 3:1.

5. A complex as claimed in claim 4, wherein the two components are present in equivalent weight ratios.

6. A complex as claimed in claim 2 wherein hyaluronic acid has weight average molecular weight ($M_w$) ranging from about $2 \times 10^5$ to about $3 \times 10^6$.

7. A complex of hyaluronic acid with carnitine or an acylcarnitine produced by the process of claim 1.

8. A complex of hyaluronic acid with L-carnitine or an acyl-L-carnitine produced by the process of claim 1.

9. A complex of hyaluronic acid with an acyl-L-carnitine selected from the group consisting of acetyl-L-carnitine, propionyl-L-carnitine and palmitoyl-L-carnitine produced by the process of claim 1.

10. A complex according to claim 7, 8 or 9, wherein hyaluronic acid has weight average molecular weight ($M_W$) ranging from about $2 \times 10^5$ to $3 \times 10^6$.

11. A complex according to claim 7, 8 or 9, wherein the two components are present in weight ratios ranging from 1:3 to 3:1.

12. A complex as claimed in claim 11, wherein the two components are present in equivalent weight amounts.

13. A process as claimed in claim 11, wherein the solvent consists of phosphate-buffered saline (PBS) at substantially neutral pH.

14. A process as claimed in claim 1, wherein the solvent consists of a mixture of ethanol and PBS.

15. A process as claimed in claim 1, wherein sonication is carried out for a time ranging from 5 to 120 minutes at 50–150 W.

16. A process as claimed in claim 15, wherein sonication is carried out for a time of 10–30 minutes.

17. A process as claimed in claim 1, wherein sonication is carried out at a temperature ranging from 15 to 50° C.

18. A process as claimed in claim 1, wherein centriftigation is carried out at about 3,000 g for a time of 5–30 minutes.

19. A complex of hyaluronic acid with a compound selected from the group consisting of L-carnitine, acetyl-L-carnitine, propionyl-L-carnitine and palmitoyl-L-carnitine produced by the process of claim 1.

20. A process for preparing a complex of hyaluronic acid with L-carnitine or an L-acylcarnitine, comprising
   (a) mixing L-carnitine or L-acylcarnitine and hyaluronic acid together in phosphate-buffered saline or a mixture of ethanol and phosphate buffered saline,
   (b) sonicating the mixture of step (a);
   (c) centrifuging the sonicated mixture of step (b) into two phases and discarding the upper phase, and
   (d) recovering the complex.

21. A complex of hyaluronic acid with a compound selected from the group consisting of L-carnitine, acetyl-L-carnitine, propionyl-L-carnitine and palmitoyl-L-carnitine produced by the process of claim 20.

22. A composition containing a complex as claimed in claim 19 or 21 together with a carrier or diluent.

23. A method of treating synovitis, gonarthrosis, Crohn's disease, rectocolitis, celiac disease, pathologies of the corneal epithelium or lower limb ulcers comprising administering a complex of claim 19 or 21.

24. An orally administrable alimentary supplement composition containing a complex as claimed in claim 19 or 21.

25. The composition according to claim 24 further containing vitamins, coenzymes, mineral substances or antioxidants.

26. A cosmetic composition containing a complex as claimed in claim 19 or 21.

* * * * *